United States Patent [19]

Thompson et al.

[11] Patent Number: 4,550,041
[45] Date of Patent: Oct. 29, 1985

[54] ARTICLE CONTAINING A THIXOTROPIC ADDITIVE AND CYANOACRYLATE MONOMER EMPLOYED FOR DEVELOPING LATENT FINGERPRINTS

[75] Inventors: Richard T. Thompson, Haddam View Heights; Philip Hinkle, West Hartford, both of Conn.; Robert B. Carroll, South Paris, Me.

[73] Assignee: Loctite Corporation, Newington, Conn.

[21] Appl. No.: 681,961

[22] Filed: Dec. 14, 1984

[60] Division of Ser. No. 743,585 filed as PCT US 84/01354, Aug. 24, 1984, published as WO 85/00963, Mar. 14, 1985, § 102(e) date Oct. 7, 1984.

[51] Int. Cl.$^4$ .......................... A61B 5/10; B41K 1/00
[52] U.S. Cl. .................................. 428/35; 118/31.5; 356/71; 427/1; 428/419; 428/516
[58] Field of Search ................. 427/1, 145; 118/31.5; 356/71; 428/35, 419, 516

[56] References Cited

U.S. PATENT DOCUMENTS

| | | | |
|---|---|---|---|
| 3,380,646 | 4/1968 | Dogen et al. | 229/57 |
| 3,502,521 | 3/1970 | Dogen et al. | 156/69 |
| 3,523,628 | 1/1968 | Colvin et al. | 222/107 |
| 3,524,537 | 8/1970 | Winter | 206/47 |
| 3,663,501 | 5/1972 | Adams et al. | 260/41 R |
| 3,839,065 | 10/1974 | Overhults et al. | 106/308 N |
| 3,935,993 | 2/1976 | Dogen et al. | 229/53 |
| 3,940,362 | 2/1976 | Overhults | 260/42.16 |
| 4,102,945 | 7/1978 | Gleave | 260/879 |
| 4,180,913 | 1/1980 | Takeuchi et al. | 433/228 |
| 4,297,383 | 10/1981 | Bourdon | 427/1 |
| 4,363,286 | 12/1982 | Leavitt | 427/1 |
| 4,379,178 | 4/1983 | Meadows et al. | 427/1 |
| 4,407,842 | 10/1983 | Shepard | 427/1 |
| 4,461,235 | 7/1984 | Morton | 427/1 |

FOREIGN PATENT DOCUMENTS 56-64933 6/1981 Japan.

OTHER PUBLICATIONS

C.A. 100(26)211222v, Oct. 1983 Takaoka Chem.
C. Abs. 100(16)122406r, Sep. 1983 Taoka Chem. Co.
Chem. Abs. 100(2)8087n, Jun. 1983 Kowa K.K., JP No. 58/108135.
Chem. Abs. 99(24)196228s, Mar. 1983 Taoka Chem. Co., JP No. 58/41068.
Chem. Abs. 96(26)218971w Taoka, Feb. 1982, JP No. 57/23666.
Chem. Abs. 96(12)80693v, Nov. 1981 Taoka, JP No. 56/142169.
Chem. Abs. 96(12)86692u, Nov. 1981 Taoka, JP No. 56/142168.
Chem. Abs. 95(18)151873z, Jun. 1981 Toagose, JP No. 56/64933.
Chem. Abs. 92(4)23838t, Aug. 1979 Matsumoto Seiyaku, JP No. 54/106426.
Chem. Abs. 91(22)176339k, May 1979 Koatsu Gas, No. 54/57539.
Chem. Abs. 88(6)38738g, Sep. 1977 Ashiwara, JP No. 52/105939.
Chem. Abs. 82(8)44562g, Feb. 1974 Toagose, JP No. 74/5728.
Chem. Abs. 71(16)71543(f) 1969 Korshak et al.
Identification News: May '82, pp. 3-5; Jun. '82, pp. 3-4; Jan. '83, pp. 9-10; Feb. '83; pp. 3-4; Feb. '83, pp. 12, 13, 15; May '83, p. 10.
Duraprint Investigators Report, Mar./Apr. '83.
Police Chronicle, May '83, "New Method of Fingerprinting . . . ".
Payton Scientific, Undated, Visuprint Advertisment.
Police Chief, Feb. '83, p. 9, Superprint TM ad.

Primary Examiner—Herbert J. Lilling
Attorney, Agent, or Firm—Walter J. Steinkraus; Eugene F. Miller

[57] ABSTRACT

Latent fingerprints are developed by exposing them to vapors generated from a thin film of a storage stable cyanoacrylate monomer and a thixotropic additive in sufficient amount to render the composition substantially non-flowable. The monomer film should have a surface area of at least 129 sq. cm.

An envelope package for the monomer composition has inner polyethylene surfaces. The envelope may be peeled open to expose the inner surfaces coated with a film of the composition.

8 Claims, 3 Drawing Figures

ARTICLE CONTAINING A THIXOTROPIC ADDITIVE AND CYANOACRYLATE MONOMER EMPLOYED FOR DEVELOPING LATENT FINGERPRINTS

BACKGROUND OF THE INVENTION

This is a division of Ser. No. 743,585 filed as PCT US 84/01354, Aug. 24, 1984, published as WO 85/00963, Mar. 14, 1985, § 102(e) date Oct. 7, 1984.

To those familiar with instant adhesives, it's no surprise that their vapors can expose fingerprints with the white residue caused by monomer "blooming". In fact, efforts to reduce this undesirable behavior date from the early days of cyanoacrylate technology.

However, it was left until much later to discover that this same process could be turned to the noble task of apprehending criminals through fingerprint identification. In 1978 the Tokyo Metropolitan Police are reported to have hosted a demonstration of cyanoacrylate fuming for development of fingerprints by criminologists of the Japanese National Police Agency. In May of 1979, Detective Inspector N. Edmunds and L. Wood of Northamptonshire (England) Police are reported to have observed that fingerprints were developed when they repaired a black plastic developing tank with Loctite Super Glue TM. Within a month, they reported their findings to a regional police conference.

Constable Paul Bourdon of the North Bay Ontario Police Force was an early practitioner of the method and invented a fuming system which generates vapor in one chamber and pumps it into another which contains the evidence under investigation. His system has been patented in the U.S. and Canada (U.S. Pat. No. 4,297,383, incorporated herein by reference).

Frank Kendall of the U.S. Bureau of Alcohol, Tobacco and Firearms, developed an improvement in the method which uses cotton treated sodium hydroxide to accelerate the generation of vapors. A description of this technique is given in Identification News, June 1982, page 3.

The use of heat to accelerate generation of cyanoacrylate vapors for fingerprint development use has also been reported. Identification News, January 1983, page 9, and May 1983, page 10.

The cyanoacrylate vapor technique has become an accepted method for fingerprint development. In several cases, identifications have been made on evidence for which no previous methods had been workable. Recently, evidence provided by this method has been accepted in a Kansas court leading to criminal conviction. Abele, Identification News, February 1983, page 12.

Recognized benefits of using cyanoacrylate monomers to develop fingerprints which have been discovered to date are as follows:

(a) Development of latent prints on objects where other methods have failed;
(b) development of prints on difficult surfaces such as polyethylene bags or electrical tapes;
(c) print images produced are easier to handle than powder-dusted prints which may blow away;
(d) large enclosed areas, such as automobile interiors can be fumed for prints.

The significant benefits of the cyanoacrylate fingerprint development technique, however, have been accompanied by other notable disadvantages. These disadvantages include the instant bonding of cyanoacrylate adhesives to skin and clothing when contacted by evidence technicians. Also, the typical low viscosity cyanoacrylate adhesive used in the prior techniques is easily spilled or dripped. This not only contributes to inadvertent bonding of clothes and skin but can also result in damage to the evidence. Initially, without acceleration of vapor generation, it has been reported that full development of a print takes at least about five hours and can take as long as 90 days.

With acceleration of vapor generation, other disadvantages have been identified as follows:

Disadvantages of Sodium Hydroxide Acceleration:
1. Sodium hydroxide is a poison and corrosive, and can cause damage to skin if not mixed wearing gloves.
2. Preparation time is substantial.
3. The technique provides a small amount of fumes for the amount of adhesive used. Most of the adhesive polymerizes, within the saturated pad or as visible white smoke, rather than being evaporated into the atmosphere within the chamber. The polymerized white smoke does not react with the latent print.
4. Fumes from the pads rise to the top of the chamber, then filter down, failing to provide uniform exposure of the objects being processed to the vapors.

Disadvantages of Heat Acceleration:
1. Temperature setting can be critical. Too hot may result in overdevelopment of the print and failure of the adhesive to polymerize within the print. Too cool may result in failure of the adhesive to be absorbed into the chamber as quickly as desired, requiring longer processing.
2. Use in smaller chambers, even in small amounts, may result in overdevelopment if the items being processed are not closely monitored.
3. Various methods of using heat as an accelerant also heat the entire chamber, affecting vinyls and plastics (especially black vinyl tapes).
4. Minor accidents involving the use of heated objects may result in burns or damage to the chamber.

SUMMARY OF THE INVENTION

The present invention is an improvement of developing latent fingerprints with cyanoacrylate vapors. The method comprises subjecting an article suspected of containing a latent fingerprint to cyanoacrylate vapors generated from a thin film of a storage-stable composition comprising a cyanoacrylate monomer and a thixotropic additive in an amount effective to render the composition substantially nonflowable on a vertical surface. This thixotropic composition is preferably also stabilized against polymerization to a degree where the adhesiveness of the composition is substantially reduced.

In a preferred embodiment of the invention, the gel composition is contained in a thin envelope or pouch which is peeled open to expose two inner surfaces coated with a thin layer of the gel. The resulting large surface area generates vapor rapidly and evenly prolonged periods of time. This rapid and sustained vapor generation can result in development of latent fingerprints which are not developed by prior art methods.

The following advantages have been identified for the inventive process over the prior art methods of generating vapors.
1. No poisons or corrosives.
2. No preparation time.

3. Produces an even amount of exposure to the adhesive evaporated within the chamber over a 20-minute plus time period.
4. Provides evaporation from a larger surface area than previous methods.
5. Room temperature operation. No critical effects of minor variations in the temperature.
6. No heat to destroy vinyls or plastics.
7. Overdevelopment does not occur in a short period of time. Items can be left in the chamber up to one hour over the amount of time required without loss of ridge detail (items, as in previous methods, should not be placed closer than 3 inches to the envelope).
8. No burns or damaged chambers.
9. No spillage of adhesive or contamination of evidence.
10. Substantially reduces complexity of cyanoacrylate use making it feasible for use in the field by minimally trained technicians.

DETAILED DESCRIPTION OF THE INVENTION

Cyanoacrylate Gel Formulation

Figure 1:
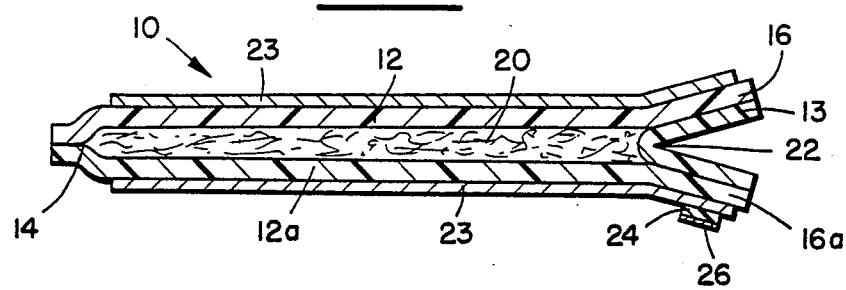
FIG. 1 is a side sectional view of a cyanoacrylate gel containing package preferred for use in the inventive method.

A high vapor pressure cyanoacrylate monomer must be utilized in order to give adequate monomer vaporization. Methyl cyanoacrylate and ethyl cyanoacrylate are the preferred monomers. Allyl cyanoacrylate and isopropyl cyanoacrylate are suitable monomers which may also be utilized alone or in a mixture.

The formulation of a storage-stable nonflowable cyanoacrylate gel has long been a difficult problem because of the ease of polymerization of the monomer. Thus, while many formulations employing typical silica thixotropes have been reported in the art, such compositions typically are intended to be utilized immediately or have been subsequently shown to have poor shelf stability. While it has been discovered that storage stable formulations of certain silicas highly treated with dimethyldichlorosilane can be made, the high degree of surface treatment so dramatically affects the thixotropic capability of the silica that nonflowable gels cannot be prepared. More recently, it has been discovered that certain uniquely treated silicas produce storage-stable nonflowable gel compositions. Compositions of cyanoacrylate monomers with these silicas, are described more fully in co-pending application U.S. Ser. No. 528,275, filed Aug. 31, 1983, now U.S. Pat. No. 4,477,607, the disclosure of which is incorporated herein by reference. The compositions of U.S. Ser. No. 528,275 are suitable for use in the inventive method and provided the initial embodiments of the gel used in the inventive method.

Working with the initial gel formulations, it was discovered that the stabilizer level could be substantially increased over that typically used in cyanoacrylate adhesive formulations. Since the fingerprints are developed by polymerization of monomer vapors, the level of stabilizer in the base composition was not critical. Therefore, the stabilizer level in the base composition could be increased to the point where adhesive bonding is significantly reduced without affecting fingerprint development performance. This is especially advantageous in fingerprint development since the possibilities of monomer contact are substantial. The monomer containers are open and have substantial surface areas (typically 2"×2" in previous methods, about 13"×4" in the preferred embodiment of the invention).

Suitably stabilizer levels are such that the well-known instantaneous fingerstick caused when fingers having cyanoacrylate monomer spilled thereon contact an article or each other does not occur for at least 10 seconds. This delay gives time to wipe off spilled material. Additionally, the stabilization allows some of the fumed silicas which previously had been discovered unsuitable for use in storage-stable cyanoacrylate adhesive formulations to be used in the fingerprint developing gels of the invention.

The thixotropic formulations used in the inventive method are substantially nonflowable as thin films on a vertical polyethylene surface.

The thixotropy of the compositions can be estimated by taking Brookfield viscosity measurements in cps (mPas) at room temperature (about 21° C.) at 2.5 and 20 RPM. Comparison of the ratios of the two measurements for various samples indicates that relative thixotropy of those samples. A sample having a 2.5/20RPM viscosity ratio (thixotropic ratio) of 1 is not thixotropic. To be suitable for use in the invention, the composition generally should have a thixotropic ratio of about 2.5 or more, preferably 3 or more.

A convenient test for determining substantial nonflowability as that term is used herein, is to spot a 0.2 gram sample of a thixotropic composition on a vertical polyethylene surface on an area of about ½"×½" (12.7 cm×12.7 cm) and observe the flow with time. If the sample flows no more than about 1" in five minutes, it will generally be suitable for use in the inventive method. Preferably the sample should not move even an inch over a several hour observation period.

Examples of suitable formulations are contained in Table I.

TABLE I

| | A | B | C | D | E | F | G |
|---|---|---|---|---|---|---|---|
| Ethyl Cyanoacrylate w/ 100 ppm SO$_2$, 100 ppm methane sulfonic acid and 1000 ppm hydroquinone | 92 | 92 | 92 | 60 | 94 | 88 | — |
| Methyl Cyanoacrylate w/ 2000 ppm methane sulfonic acid and 1000 ppm hydroquinone | — | — | — | — | — | — | 88 |
| Aerosil R972[1] | 8 | — | — | — | — | — | — |
| Aerosil R976[1] | — | 8 | — | — | — | — | — |
| Aerosil R805[1] | — | — | 8 | — | — | — | — |
| Aerosil R200[1] | — | — | — | — | 6 | — | — |
| Cabosil N70-TS[2] | — | — | — | — | — | 6 | 6 |
| Polyvinylidine Fluoride[3] | — | — | — | 40 | — | — | — |
| Polymethylmethacrylate | — | — | — | — | — | 6 | 6 |
| Room Temp. Visc. 2.5 RPM (cps × 10$^3$) | 22 | 12 | 80 | 100 | 640 | 96 | — |
| Thixotropic Ratio 2.5 RPM/ 20 RPM | 3.0 | 3.0 | 5.7 | 5.3 | 7.3 | 5.7 | — |

[1]Aerosil is a trademark of DeGussa Corp. R972, R976, R805, and 200 are fumed silicas with respective treatments: dimethyldichlorosilane, octyltrimethoxysilane, and untreated.
[2]Cabosil is a trademark of Cabot Corp. N70-TS is fumed silica treated with polydimethylsiloxane.
[3]See U.S. Pat. No. 4,105,775.

The various formulations have different monomer evaporation characteristics depending on thixotrope and level. Formulations such as C and E are preferred for evaporation charactertistics because they give faster evaporation rates and almost total evaporation at room temperature before polymerization from thin films on polyethylene. Composition D had the slowest evaporation and lowest total evaporation, presumably because of the high polymer content.

Generating The Vapors

In order to obtain rapid and uniform vapor generation at room temperature, it is desirable that the monomer be distributed over a large surface area. Whereas development techniques using pourable liquid monomers must contain the monomer in a bowl on a horizontal surface, the nonflowable formulations used in the inventive method do not have to be contained. They may be thinly spread on vertical surfaces, e.g., on a sheet of paper or plastic film hung on a wall, without fear of damage to evidence or personnel.

Figure 2:
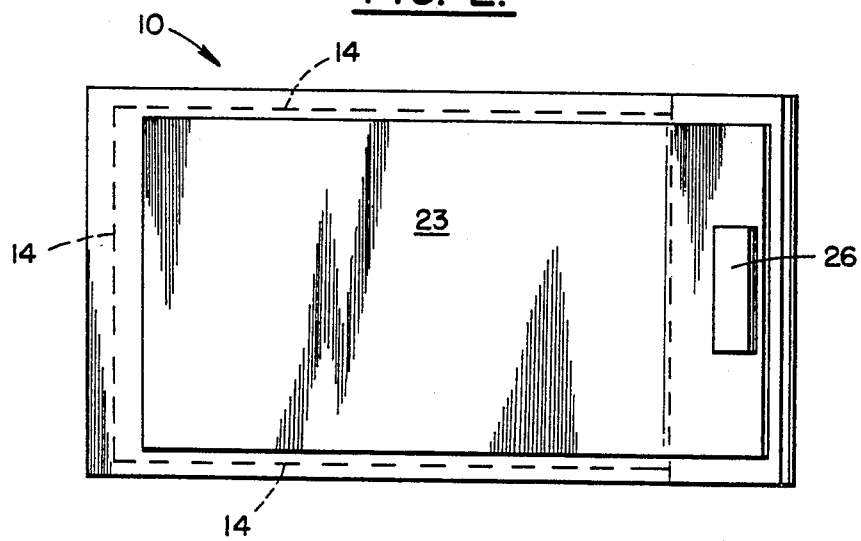
FIG. 2 is a bottom plan view of the package of FIG. 1.
Figure 3:
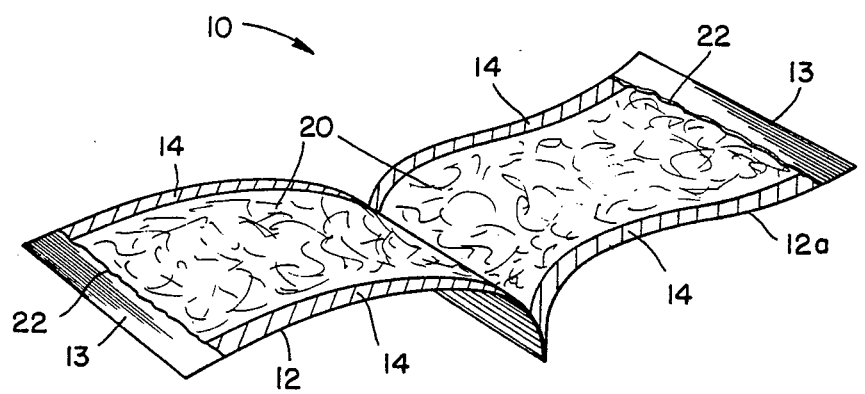
FIG. 3 is a pictorial view of the opened package showing cyanoacrylate coated inner surfaces exposed to the air for vapor generation.

A preferred package for the fingerprint developing gels is shown in FIGS. 1-3. The package generally designated by the numeral 10 is an envelope constructed from three sheets, 12, 12a and 13 of a laminate material having a polyethylene inner surface. The laminate is preferably a paper/polyethylene/aluminum/-polyethylene laminate material. A bonding primer between the various layers is preferably included so that the material does not delaminate when the envelope is peeled open. Three heat sealed edges 14 bond sheets 12 and 12a together. Sheet 13 is heat sealed between the end flaps 16 and 16a at the fourth end of sheets 12 and 12a, thereby forming a closed envelope structure with separable but sealed end flaps 16 and 16a. Inside the envelope is a thin layer of the gel cyanoacrylate formulation 20. To open and use, flap 16 and 16a are pulled apart as shown in FIG. 1 and sheet 13 is torn along the fold line 22. To facilitate substrate failure along the side edges 14, the central outer portions of sheets 12 and 12a may be reinforced by an additional layer of tape or label material 23. Sheets 12 and 12a are then peeled back as shown in FIG. 3 to open the package 10 and expose the cyanoacrylate gel 20 to the air. The gel sticks to the inner surfaces of both sheets 12 and 12a so that a maximum surface area of cyanoacrylate monomer is exposed. It is recommended that the package when opened provide a monomer coated surface area of at least 20 sq. in. (129 sq. cm.), preferably 40 sq. in. (258 sq. cm.) or more.

Optionally package 10 may also be supplied with a strip 24 pressure sensitive adhesive located on the outer surface of flap 16a. Strip 24 is covered with a release paper 26 which may be pulled off when the package is to be used. The exposed adhesive layer 24 may then be used to adhere the open package to a desired surface such as a wall or window. Since the cyanoacrylate monomer is in gelled form it does not run off sheets 12 and 12a even when the open package is hung vertically or upside down.

Although the seal is broken when the package is first opened, the package may be closed after use and reused over several weeks before the monomer is completely polymerized or vaporized.

Developing The Fingerprints

For small portable evidence items a fuming chamber such as an aquarium fitted with a lid may be used. The lid contains a hanging device such as a clothes hanger or alligator clips from which the evidence is suspended. A preferred envelope 10 contains about 3-4 grams of a gel such as in formulation F in a 6½"×4" enclosure. When peeled open the surface area is approximately 13"×4". This preferred envelope is referred to hereinafter as the "pouch".

Items to be processed are distributed evenly throughout the chamber. A dish containing warm water is placed within the chamber. For larger chambers more than one container with water may be required. The pouch is then peeled apart, immediately placed within the chamber (at least 3 inches from the items being processed), and the chamber then sealed. Fumes are not visible, but are present in very high concentration within minutes. Excellent results can be obtained using one pouch for 20 minutes for every two and one half gallons of chamber. The amount of time used for processing larger chambers can be estimated using this as a guide (i.e., 5 gallons for 40 minutes, ten gallons for 80 minutes with one pouch, or 40 minutes with two pouches, etc.). Using more than one pouch is recommended for chambers larger than twenty gallons.

Suspending the pouches from the top of the chamber may provide better results in the larger chambers (20 gallons and larger) as the cyanoacrylate ester molecules are heavier than air. The addition of water to the chamber (for humidity) is more critical than with other methods. Water containers should be placed so as to provide even dispersal of the humidity throughout the interior of the chamber. Overdevelopment of the prints can occur if the processing time extends beyond twice the time recommended above. Monitoring of the processing is highly recommended.

When the fuming process is complete, care should be taken when opening the chamber so as to prevent exposure to the cyanoacrylate ester fumes. Upon removing the pouch from the chamber, pressing of the two panels back together will stop the release of the fumes. The pouch can be reused when needed, often for more than ten hours of total processing time per pouch. Once the original pouch seal is broken, the pouch should be used within 2 weeks, or reduced strength due to slow evaporation may occur. The pouch should be replaced when more than 75% of the gel is observed to have dried.

Due to the ease of use and lack of liquid glue, the pouch is better suited for field use than the previously encountered methods of development. The pouch can be used in portable chambers, automobiles, and larger areas by using the guidelines previously described for amount of pouches, size of chamber, and amount of time for development. The addition of water for humidity is also a requirement for field use.

Most automobiles can be processed using three or four pouches evenly dispersed throughout the interior of the vehicle. Development time depends on the size of the vehicle, but in most cases is complete within two or three hours. The addition of several beakers of warm water usually provides sufficient humidity. Placement of the vehicle inside on cold days and in the sun on warm days will assist in lessening the effects of cold temperatures on the processing time.

Rooms can be processed using one pouch for every fifteen square feet of floor space (based on eight foot ceilings). Examples are: 8×10 room=five pouches; 12×12 room=10 pouches. Development may take as long as eight hours. Water containers should be placed so as to provide even dispersal of the humidity throughout the room.

Suspending the pouches above and in the area suspected of containing prints may shorten the processing time. Addition of a small object with test prints within the chamber is recommended. The item should be visible from the exterior of the chamber if possible. When opening the chamber, allow sufficient time for the fumes to dissipate prior to entering. Organic vapor absorbing masks or respirators are recommended for entering room's in order to open windows, doors, etc., for ventilation.

The following case histories illustrating use and comparative advantages of the inventive product and method have been provided by the Torrance California Police Department. The used is the preferred envelope described above.

CASE #1

On Feb. 26, 1984 at approximately 0130 hours, patrol units of the Torrance, Calif. Policy Department were advised of a drive-by shooting which had just occurred in a neighboring city. Units were advised that one person had been shot, and a description of the suspect vehicle and three suspects within. Approximately five minutes after the broadcast, a Torrance Police patrol unit observed the suspect vehicle entering the city of Torrance, from the city in which the shooting had occurred. A subsequent stop of the vehicle resulted in the detention of three possible suspects. A search of the vehicle revealed a Charter Arms .38 special caliber revolver with blue steel finish, hidden in a trash container within the vehicle. The three occupants of the vehicle were subsequently arrested for attempted homicide.

Preliminary investigation had revealed that it was unknown which suspect had fired the shot from the vehicle. Physical evidence, therefore, became critical. In addition to other evidence collected from the suspects and the vehicle, crime scene investigation personnel recovered the weapon. The weapon was then transported to the Torrance Police Department for processing, at the request of the police agency within whose city the shooting had occurred.

For the past several years since the introduction of fuming for latent prints with cyanoacrylate esters, it had been standard operating procedure to process most all firearms for latent prints with the fumes from cyanoacrylate adhesive. The process utilized at Torrance was the use of cotton pads treated with sodium hydroxide, to which three grams of the adhesive is applied. In following these procedures, the weapon was placed within a two and one half gallon aquarium, suspended from a rod attached to the top of the chamber. Two 2"×2" cotton pads (pretreated) were placed within the chamber, in addition to a small cup of water. Approximately three grams of methyl cyanoacrylate ester adhesive were placed on each pad, and the chamber was sealed. Within five seconds the pads were observed to commence fuming, and were observed to continue fuming for approximately thirty seconds.

After having been within the chamber for over an hour, the weapon was removed and examined. Using normal and oblique light, no identifiable latent prints were observed, and very little ridge detail was apparent. Due to the seriousness of the crime, it was decided to re-process the weapon with a cyanoacrylate gel containing pouch.

The weapon was placed within the same chamber, again suspended from the top of the chamber. A fresh cup of water was added, and the cotton pads were removed. The pouch was opened and placed within the bottom of the chamber, and the chamber then sealed. After twenty minutes the chamber was opened and the weapon removed. Upon examination of the right side plate of the weapon, a fingerprint was observed to be white and of value. Several other latents were observed, but were determined to be of no value. A subsequent comparison of the latent print to the inked print cards of the three suspects resulted in an identification. As the comparison had been made from the latent still on the weapon, attention was directed to the recovery and preservation of the latent. The latent was photographed prior to processing with powder and tape. The latent was then dusted using Lightning black powder and a zephyr brush. The latent was then lifted a total of eighteen times. Upon examination of the lifts, it was determined that the fifth lift contained the best quality ridge detail. It was also noted that the latent on the weapon still contained more ridge detail than the best lift.

Based on experiments with the pouch, and past experience in the use of cotton pads treated with sodium hydroxide, it is believed that the treated cotton pads failed due to the small amount of monomer fumes that were released into the atmosphere of the chamber. The pouch product provided maximum evaporation of the adhesive within the chamber, thereby providing results where the treated cotton pads failed.

It has been observed that in many cases the latent on the object that has been subjected to the cyanoacrylate ester adhesives is of better quality than most of the lifts obtained with the various powders and tapes. It is strongly recommended that latents obtained using any of the various methods of applying the fumes from the adhesive be photographed prior to application of the powder.

CASE #2

On Mar. 4, 1984 at 1400 hours patrol units of the Torrance Police Department were advised of an auto theft which had just occurred within the city. Units were advised that the vehicle was a 1976 Ford pick-up green in color, having a green camper shell, and of the vehicle license plate. Within 30 seconds of the broadcast, two patrol units enroute to another call observed the suspect vehicle being driven by the suspect. Units attempted to stop the vehicle, and a pursuit ensued. As with most pursuits, this one was brief, covering a distance of five blocks where the suspect lost control of the vehicle, collided with a building, causing major damage. The suspect exited the vehicle, and a foot pursuit then ensued. The suspect was chased over a distance of four blocks, where he was subsequently apprehended.

Although observed by two officers within the vehicle, suspect identification by latent prints in addition to officers observations provides very strong evidence. It is therefore policy to process the vehicles in these situations for latent print evidence. Latent lifts were obtained from the passengers window point of entry, and an ashtray removed by the suspect to gain access to the ignition from under the dash. It was observed that the suspect had removed the victims ignition lock and replaced it with an ignition lock for which the suspect had a key. The suspects ignition lock was recovered from the vehicle and transported to the crime scene investigation facility for processing.

The ignition lock was placed within a two and one half gallon aquarium containing a small cup of water and an opened pouch. The chamber was sealed for twenty minutes, after which the ignition lock was removed and examined. Two latent print were observed to be white and of value. One of the latent prints was observed on the base of the ignition lock, the other on the faceplate where the key is inserted. The latents were photograph and then powdered using Lightning black powder and a zephyr brush. Six latent lifts were obtained, and again it was noted that the latents (three lifts per latent) on the ignition lock were of better quality than the lifts. Comparison of the latent on the face of the ignition lock to the suspect inked prints resulted in an identification. Identifications were also made on the lifts obtained from the window and ashtray.

CASE #3

On Mar. 8, 1984 at 0120 hours units of the Torrance Police Department were advised of a shooting that had just occurred outside a local bar within the city. Information received indicated that four male suspects in a small white vehicle had driven through the parking lot outside the bar, and fired two shots at a woman, hitting her both times. Units arriving at the scene were advised by witnesses that the occupants of the vehicle had been inside the bar prior to the shooting. One of the suspects had approached the victim in the bar and asked her to dance, and was turned down. Shortly thereafter the victim exited the bar with several friends, and was approached in the parking lot by a small white vehicle containing the four suspects. The victim observed one of the suspects holding a handgun and turned and ran, at which time two shots were heard, the victim falling to the ground. The suspects then fled the location in the vehicle. The victim had received two gunshot wounds, one to the right calf, the other to the center back, severing her spine.

Information regarding the incident was broadcast to Torrance Police units and neighboring agencies. Fifteen minutes after the shooting, a patrol unit from the Los Angeles County Sheriff's Department observed the suspects in the vehicle mobile, and with the assistance of a Torrance unit nearby stopped the suspects. The suspects were placed under arrest for attempted murder. A subsequent search of the vehicle revealed two weapons, a Charter Arms .357 magnum revolver with blue steel finish, and an Enforcer pistol, .30 caliber M-1 carbine with a full 30 round magazine. The weapons were recovered and transported to the crime scene investigation facility for processing.

The .357 caliber revolver was placed within a two and one half gallon aquarium with a small cup of water and one opened pouch, the chamber then sealed. The Enforcer carbine was placed within a ten gallon aquarium with a cup of water and one opened pouch, the chamber then sealed. After twenty minutes the revolver was removed from the chamber and examined. No white latents were observed with direct lighting. Upon examination with oblique light, three latent prints were observed, one of which was determined to be of value. The latent print of value was observed on the right side plate below the serial number. Close examination of the weapon revealed a thin coat of oil on the surface containing the latent. Previous experience with oil coated surfaces had shown that application of powder would succeed in destruction of the latent. Photographs were then obtained of the latent. A subsequent comparison of the latent on the revolver resulted in an identification of one of the four suspects.

The revolver was then properly packaged in order to preserve the latent remaining on the weapon. The Enforcer carbine was removed from the chamber after forty minutes. No identifiable latent prints were observed on the weapon. Examination of the 30 round magazine revealed numerous latents, two of which were determined to be of value. Photographs were obtained of these latents, which were subsequently powdered and lifted using the previously described powder. One of the latents was lifted ten times, the third lift providing the best ridge detail. It was noted that the third lift provided better contrast than the same latent still on the magazine. The second latent was lifted five times. The second lift provided the best ridge detail. It was noted that the same latent still on the magazine was of better quality than any of the lifts obtained from it. Subsequent comparison of these patent prints to the suspects resulted in another suspect identified.

It was further determined through physical evidence that the revolver had been the weapon used in the shooting. In addition to the other evidence collected from the suspects and from the scene, the suspect who had been identified to the revolver with the latent print was determined to have fired the weapon. The results of the physical evidence resulted in a filing of attempted murder on this suspect.

We claim:

1. An article for rapid room temperature generation of cyanoacrylate monomer vapors comprising an envelope containing a storage stable composition of a cyanoacrylate monomer and a thixotropic additive in an amount effective to render the composition substantially non-flowable on a vertical surface, the envelope defined by a pair of opposed sheets of a material having an inner plastic film surface, said sheets being sealed together along the edges thereof in a manner adapted to permit separation of the sheets by tearing or peeling along the edges thereof so as to expose the inner sheet surfaces coated with a film of said composition.

2. An article as in claim 1 wherein said two envelope defining sheets are rectangular sheets heat sealed together along three edges thereof and having a third sheet interposed between said first two sheets along the fourth edges thereof, said third sheet having a plastic film inner surface, and the third sheet being interposed between the first two sheets in folded form such that its inner plastic film surface contacts and is heat sealed to the respective fourth edges of the first two sheets.

3. An article as in claim 2 wherein the sheet material is a laminate of paper/polyethylene/aluminum/polyethylene.

4. An article as in claim 1 wherein the inner composition coated inner sheet surfaces have a combined area of at least 20 sq. in.

5. An article as in claim 4 wherein the said combined surface area is at least 40 sq. in.

6. An article as in claim 1 wherein one of said opposed sheets includes a portion on the outer surface thereof having a layer of a pressure sensitive adhesive thereon whereby the article may be affixed to a vertical surface.

7. An article as in claim 1 wherein said inner plastic film surface is polyethylene.

8. An article as in claim 2 wherein said inner surfaces of said first two sheet and said third sheet are all polyethylene.

* * * * *